United States Patent
Lorenz

(10) Patent No.: US 6,344,214 B1
(45) Date of Patent: Feb. 5, 2002

(54) METHOD FOR RETARDING AND AMELIORATING FEVER BLISTERS AND CANKER SORES

(75) Inventor: R. Todd Lorenz, Kailua-Kona, HI (US)

(73) Assignee: Cyanotech Corporation, Kailua-Kona, HI (US)

(*) Notice: Subject to any disclaimer, the term of this patent is extended or adjusted under 35 U.S.C. 154(b) by 0 days.

(21) Appl. No.: 09/459,516

(22) Filed: Dec. 13, 1999

(51) Int. Cl.$^7$ .................... A61K 35/70; A01N 63/04
(52) U.S. Cl. .................. 424/451; 424/435; 514/886; 514/887; 514/900; 568/378
(58) Field of Search ................. 424/435, 451, 424/195.16; 514/886, 887, 900; 568/378

(56) References Cited

U.S. PATENT DOCUMENTS 5,527,533 A * 6/1996 Tso et al. ............... 424/422
5,942,245 A * 8/1999 Katinger et al. .......... 424/450

OTHER PUBLICATIONS

Bendich, Adrianne, *Carotenoids and the Immune Response*, pp. 112–115.

Haruni et al., *Astaxanthin, a Carotenoid without Vitamin A Activity, Augments Antibody Responses in Cultures Including T–helper Cell Clones and Suboptimal Doses of Antigen*, 1995, pp. 24922483–.

Jyonouchi et al, *Effect of Carotenoids on In Vitro Immunoglobulin Production by Human Peripheral Blood Mononuclear Cells*, 1995, pp. 171–183.

Kurashige et al, *Inhibition of Oxidative Injury of Biological Membranes by Astaxanthin*, 1990, pp. 27–38.

Miki, Vataru, *Biological Functions and Activities of Animal Carotenoids*, 1991, pp. 141–146.

Nakagawa et al., *Inhibition by B–Carotene and Astaxanthin of NADPH–Dependent Microsomal Phospholipid Peroxidation*, 1996, pp. 345–355.

O'Connor et al., *Modulation of UVA light–induced oxidative stress by B–carotene, lutein and astaxanthin in cultured fibroblasts*, 1998, 226–230.

Oshima et al., *Inhibitory Effect of B–Carotene and Astaxanthin on Photosensitized Oxidation of Phospholipid Bilayers*, 1993, pp. 607–615.

Palozza et al., *Astaxanthin and Canthaxanthin Are Potent Antioxidants in a Membrane Model*, 1993, pp. 291–295.

Savoure et al., *Vitamin A Status and Metabolism of Cutaneous Ployamines in the Hairless Mouse After UV Irradiation Action of V–Carotene and Astaxanthin*, 1994, pp. 79–86.

Tanaka et al., *Chemoprevention of mouse urinary bladder carcinogenesis by the naturally occurring carotenoid astaxanthin*, 1994, pates 15–19.

Tanaka et al., *Suppression of azoxymethane–induced rat colon carcinogenesis by dietary administration of naturally occurring xanthophyll astaxanthin and canthaxanthin during the postinitiation phase*, 1995, pp. 2957–2963.

Tanaka et al., *Chemoprevention of Rat Oral Carcinogenesis by Naturally Occurring Xanthophylls, Astaxanthin and Canthaxanthin*, 1995, pp. 4059–4064.

* cited by examiner

Primary Examiner—Thurman K. Page
Assistant Examiner—Liliana Di Nola-Baron
(74) Attorney, Agent, or Firm—Devine, Millimet & Branch PA; Paul C. Remus; Kristin Kohler

(57) ABSTRACT

Astaxanthin is a potent antioxidant, over 500 times more powerful than Vitamin E and 10 times stronger than other carotenoids such as zeaxanthin, lutein, canthaxanthin and beta-carotene. Astaxanthin has also been shown to enhance and modulate the immune system and diminish the damaging effects of UVA sunlight. Disclosed is a method for retarding and ameliorating fever blisters (cold sores) and canker sores. The method comprises administering a source of astaxanthin in a therapeutically effective amount to prevent, retard and ameliorate fever blisters and canker sores. The astaxanthin may be administered orally, topically, or in a combination of oral and topical dosage.

12 Claims, No Drawings

METHOD FOR RETARDING AND AMELIORATING FEVER BLISTERS AND CANKER SORES

FIELD OF THE INVENTION

This invention relates to the treatment and prevention of fever blisters (cold sores) and canker sores. More particularly the invention relates to a method for treatment and prevention of fever blisters and canker sores using, as a basis, the protective properties of astaxanthin. Most particularly the invention relates to treatment and prevention of fever blisters and canker sores using orally and/or topically administered astaxanthin.

BACKGROUND OF THE INVENTION AND PRIOR ART

Fever blisters and canker sores are two of the most common disorders of the mouth, causing discomfort and annoyance to millions of Americans. Both cause small sores to develop in or around the mouth, and often are confused with each other. Canker sores occur only inside the mouth, on the tongue and the inside linings of the cheeks, lips and throat. Fever blisters, also called cold sores, usually occur outside the mouth—on the lips, chin, cheeks or in the nostrils. When fever blisters do occur inside the mouth, it is usually on the gums or the roof of the mouth. Inside the mouth, fever blisters are smaller than canker sores, heal more quickly, and often begin as a blister. Both canker sores and fever blisters have plagued mankind for thousands of years. Scientists at the National Institute of Dental Research, one of the federal government's National Institutes of Health, are seeking ways to better control and ultimately prevent these and other oral disorders.

Fever Blisters

Today fever blisters still occur in epidemic proportions, about 100 million episodes of recurrent fever blisters occur yearly in the United States alone. An estimated 45 to 80 percent of adults and children in this country have had at least one bout with the blisters. Fever blisters are caused by a contagious virus called herpes simplex of which there are two types. Type 1 usually causes oral herpes, or fever blisters. Type 2 usually causes genital herpes. Although both type 1 and type 2 viruses can infect oral tissues, more than 95 percent of recurrent fever blister outbreaks are caused by the type 1 virus. Herpes simplex virus is highly contagious when fever blisters are present, and the virus frequently is spread by kissing. Children often become infected by contact with parents, siblings or other close relatives who have fever blisters. A child can spread the virus by rubbing his or her cold sore and then touching other children. About 10 percent of oral herpes infections in adults result from oral-genital sex with a person who has active genital herpes (type 2). These infections, however, usually do not result in repeat bouts of fever blisters. Most people infected with the type 1 herpes simplex virus became infected before they were 10 years old. The virus usually invades the moist membrane cells of the lips, throat or mouth. In most people, the initial infection causes no symptoms. About 15 percent of patients, however, develop many fluid-filled blisters inside and outside the mouth 3 to 5 days after they are infected with the virus. These may be accompanied by fever, swollen neck glands and general aches. The blisters tend to merge and then collapse. Often a yellowish crest forms over the sores, which usually heal without scarring within 2 weeks.

The herpes virus, however, stays in the body. Once a person is infected with oral herpes, the virus remains in a nerve located near the cheekbone. It may stay permanently inactive in this site, or it may occasionally travel down the nerve to the skin surface, causing a recurrence of fever blisters. Recurring blisters usually erupt at the outside edge of the lip or the edge of the nostril, but can also occur on the chin, cheeks, or inside the mouth. The symptoms of recurrent fever blister attacks usually are less severe than those experienced by some people after an initial infection. Recurrences appear to be less frequent after age 35. Many people who have recurring fever blisters feel itching, tingling or burning in the lip 1 to 3 days before the blister appears.

Several factors weaken the body's defenses and trigger an outbreak of herpes. These include emotional stress, fever, illness, injury and exposure to sunlight. Many women have recurrences only during menstruation. One study indicates that susceptibility to herpes recurrences is inherited. Research is under way to discover exactly how the triggering factors interact with the immune system and the virus to prompt a recurrence of fever blisters. Currently there is no cure for fever blisters. Some medications can relieve some of the pain and discomfort associated with the sores, however. These include ointments that numb the blisters, antibiotics that control secondary bacterial infections, and ointments that soften the crests of the sores.

There is no vaccine for herpes simplex virus available to the public. Many research laboratories, however, are working on this approach to preventing fever blisters. For example, scientists at the National Institute of Dental Research and the National Institute of Allergy and Infectious Diseases have developed a promising experimental herpes vaccine. In tests on laboratory mice, the vaccine has prevented the herpes simplex virus from infecting the animals and establishing itself in the nerves. Although these findings are encouraging, the scientists must complete more animal studies on the safety and effectiveness of the vaccine before a decision can be made whether to test it in humans. The vaccine would be useful only for those not already infected with herpes simplex virus.

Scientists at the National Institute of Dental Research have confirmed that sun screen on the lips can prevent sun-induced recurrences of herpes. They recommend applying the sun screen before going outside and reapplying it frequently during sun exposure. The researchers used a sun block with a protection factor of 15 in their studies. Little is known about how to prevent recurrences of fever blisters triggered by factors other than sunlight. People whose cold sores appear in response to stress should try to avoid stressful situations. Some investigators have suggested adding lysine to the diet or eliminating foods such as nuts, chocolate, seeds or gelatin.

Researchers are working on several approaches to preventing or treating fever blisters. As mentioned earlier, they are trying to develop a vaccine against herpes simplex virus. Several laboratories are developing and testing antiviral drugs designed to hamper or prevent fever blister outbreaks. Researchers also are trying to develop ointments that make it easier for antiviral drugs to penetrate the skin. Acyclovir is an antiviral drug that prevents the herpes Simplex virus from multiplying. The U.S. Food and Drug Administration has approved the drug for use in treating genital herpes, and is considering its approval for use in treating oral herpes. Researchers have found that acyclovir taken in pill form reduces the symptoms and frequency of fever blister recurrences in some patients. In one study, 50 percent of patients who took four acyclovir pills daily for 4 months had no fever blister outbreaks. Before taking the drug, they had an average of one recurrence every 2 months. In separate studies, pills taken at the onset of symptoms, or acyclovir cream applied to the blisters or to areas of the lip that tingled or itched were found to be only minimally effective. The long-term effects of daily oral doses of acyclovir are not known, nor are the effects the drug might have on an unborn child.

Basic research on how the immune system interacts with herpes simplex viruses may lead to new therapies for fever blisters. The immune system uses a wide array of cells and chemicals to defend the body against infections. Scientists are trying to identify the immune components that prevent recurrent attacks of oral herpes. Scientists are also trying to determine the precise form and location of the inactive herpes virus in nerve cells. This information might allow them to design antiviral drugs that can attack the herpes virus while it lies dormant in nerves. In addition, researchers are trying to understand how sunlight, skin injury and stress can trigger recurrences of fever blisters to block reactivation of the virus (U.S. Department of Health and Human Services. National Institutes of Health National Institute of Dental Research, NIH Publication No. 92-247).

Canker Sores

Canker sores (Recurrent Aphthous Stomatitis, aphthous ulcers, oral ulcers) are mouth sores which plague millions of people. For some, canker sores are a minor nuisance and for others are constant sources of pain and discomfort. It appears that diet may influence episodes of cander sores as some people have allergies to certain foods and consumption of these foods can lead to canker sores. Studies show that elimination of these offending foods can sometimes reduce the number of canker sore episodes a person experiences. Wray, Vlagopoulos, and Siraganian (1982), have showed a relationship between buckwheat, whole wheat, rye barley, chocolate, nuts shellfish, soy, tomatoes, apples, and cheese and the incidence of canker sores. In a separate study, Hay and Reade (1984) demonstrated that diets that lacked certain foods resulted in improvements in 43 percent of the patients involved in the study. Food eliminated in these diets included: figs, cheese, tomatoes, lemon, venegar, French mustard, pineapples, apples, milk, wheat, and flour. Chocalate, in particular, is a problem for some people and often leads to canker sores.

Recurrent canker sores afflict about 20 percent of the general population and are usually found of the movable parts of the mouth such as the tongue or the inside linings of the lips and cheeds. They begin as small oval or round reddish swellings, which usually burst within a day. The ruptured sores are covered by a thin white or yellow membrane and edged by a red halo. Generally, they heal within 2 weeks. Canker cores range in size from and eighth of an inch wide in mild cases to more than inch wide in severe cases. Severe canker may leave scars. Fever is rare, and the sores are rarely associated with other diseases. Usually a person will have only one or a few canker sores at a time. Most people have their first bout with canker sores between the ages of 10 and 20 but children as young as 2 may develop the condition. The frequency of canker sore recurrences varies considerably, some people have only one or two episodes a year while others may have a continuous series of canker sores.

The cause of canker sores is not well understood, but is not contagious. More than one course is likely, even for individual patients. Canker sores do not appear to be caused by biruses or bacteria, although an allergy to a type of bacterium commonly found in the mouth may trigger them in some people. The sores may be an allergic reaction to certain foods. In addition, there is research suggesting that canker sores may be caused by a faulty immune system that uses the body's defenses against disease to attack and destroy the normal cells of the mouth or tongue. British studies show that, in about 20 percent of patients, canker sores are due partly to nutritional deficiencies, especially lack of vitamin B 12, folic acid and iron. Similar studies performed in the United States, however, have not confirmed this finding. In a small percentage of patients, canker sores occur with gastrointestinal problems, such as an inability to digest certain cereals. In these patients, canker sores appear to be part of a generalized metabolic or immune disorder of the digestive tract.

Female sex hormones apparently play a role in causing canker sores, thus women are more likely than men to have recurrent canker sores. Many women have bouts of the sores only during certain phases of their menstrual cycles and experience improvement or remission of their canker sores during pregnancy. Researchers have used hormone therapy successfully in clinical studies to treat some women. Both emotional stress and injury to the mouth can trigger outbreaks of canker sores, but these factors probably do not cause the disorder. Genetic studies show that susceptibility to recurrent outbreaks of the sores is inherited in some patients. This partially explains why family members often share the disorder.

Most doctors recommend that patients who have frequent bouts of canker sores undergo blood and allergy tests to determine if a nutritional deficiency, allergy or some other preventable cause results in their sores. Vitamins and other nutritional supplements often prevent recurrences or reduce the severity of canker sores with patients that have a nutritional deficiency. Some patients with food allergies can reduce the frequency of canker sores by avoiding those foods. Patients with canker sores must avoid abrasive foods such as potato chips that can stick in the cheek or gum and aggravate the sores. Care must be taken when brushing teeth not to stab the gums or cheek with a toothbrush bristle and acidic and spicy foods must be avoided.

There are several treatments for reducing the pain and duration of canker sores for patients whose outbreaks cannot be prevented. These include numbing ointments such as benzocaine, which are available in drug stores without a prescription. Anti-inflammatory steroid mouth rinses or gels can be prescribed for patients with severe sores. Mouth rinses containing the antibiotic tetracycline may reduce the unpleasant symptoms of canker sores and speed healing by preventing bacterial infections in the sores. Clinical studies at the National Institute of Dental Research have shown that rinsing the mouth with tetracycline several times a day usually relieves pain in 24 hours and allows complete healing in 5 to 7 days. The U.S. Food and Drug Administration warns, however, that tetracycline given to pregnant women and young children can permanently stain youngsters' teeth. Both steroid and tetracycline treatments require a prescription and care of a dentist or physician. Patients with severe recurrent canker sores may need to take steroid or other immunosuppressant drugs orally. These potent drugs can cause many undesirable side effects, and should be used only under the close supervision of a dentist or physician.

Researchers are trying to identify the malfunctions in patients' immune systems that make them susceptible to recurrent bouts of canker sores. By analyzing the blood of people with and without canker sores, scientists have found several differences in immune function between the two groups. Whether these differences cause canker sores is not yet known. Researchers also are developing and testing new drugs designed to treat canker sores. Most of these drugs alter the patients' immune function. Although some of the drugs appear to be effective in treating canker sores in some patients, the data are still inconclusive. Until these drugs are proven to be absolutely safe and effective, they will not be available for general use (U.S. Department of Health and Human Services. National Institutes of Health National Institute of Dental Research, NIH Publication No. 92–247).

Carotenoids

Carotenoids are a family of over 700 natural lipid-soluble pigments that are only produced by phytoplankton, algae, plants, and a limited number of fungi and bacteria. The carotenoids are responsible for the wide variety of colors they provide in nature, most conspicuously in the brilliant yellow and red colors of fruits and leaves. In plants and algae, carotenoids are a vital participant in the photosynthetic process along with chlorophyll and other light-harvesting pigments.

While some animals are able to alter carotenoids into other forms, they still must obtain them from their diet. The pink flamingo, for instance, filters Spirulina or other algae from bodies of water and converts the yellow carotenoids, beta-carotene and zeaxanthin, into the pinkish-red carotenoids astaxanthin and canthaxanthin. These red carotenoids are then deposited into the feathered plumage and elicit the striking color of this bird.

Carotenoids, especially astaxanthin, are distinguished by their capacity to interact with chemically reactive species of oxygen known as singlet oxygen and free radicals. Astaxanthin is actually quite common in nature, especially in the marine environment. Various animals, in addition to the flamingo, have adapted to exploit the potent antioxidant properties of carotenoids. One familiar example is seen in the cold water fish that selectively accumulate astaxanthin from their diet and deposit it in their flesh to protect lipid tissues from peroxidation, a harmful form of oxidation. These animals include salmon and trout, as well as shrimp, lobsters and crayfish, and it is the astaxanthin that provides the pinkish-red hue to the flesh of these animals. The animals obtain astaxanthin in their diet from zooplankton, insects or crustaceans that have accumulated astaxanthin from phytoplankton.

Algae

One of the more common sources of astaxanthin is the alga *Haematococcus pluvialis*, also referred to as *Haematococcus lacustris* or *Sphaerella lacustris*, which is a ubiquitous green alga of the order Volvocales, family Haematococcaceae. It is now known that the alga occurs in nature worldwide, where environmental conditions for its growth are favorable. While Haematococcus occurs in nature worldwide, it is most often found in cooler pools of fresh water such as garden birdbaths. A close relative of Haematococcus is known as "snow algae" and can often be seen as the blood-red layer on ice banks and snow fields in springtime.

Under nutrient-rich conditions, Haematococcus is motile and utilizes the available nitrate, phosphate, and other nutrients to grow and reproduce. However, when nutrients become limiting or the pool begins to dry the alga form a protective cell wall and encyst. Massive amounts of the compound astaxanthin are produced, and the cells undergo a dormant stage until the next influx of water and nutrients. Cells can remain viable in this encysted stage with its protective astaxanthin for decades. Red cysts are significantly more resistant to photoinhibition and oxygen radicals than green cells, suggesting significant protective roles for astaxanthin (Kobayashi et al., 1992a). Additionally, the carotenoid fraction of green vegetative cells consists of mostly lutein (75–80%) and β-carotene (10–20%). Whereas in red cysts, the predominate carotenoid is astaxanthin (Renstrom et al., 1981).

As stated above, while natural sources of astaxanthin are quite numerous, nearly all provide very low concentrations. By far, the green algae *Haematococcus pluvialis* provides the most concentrated natural source of astaxanthin known, from 10,000–40,000 ppm (mg/kg) astaxanthin in addition to other important carotenoids such as beta-carotene, lutein and canthaxanthin. Other sources of astaxanthin include processed crustacean wastes from krill, shrimp, crab and crawfish, and the fermentative yeast *Phaffia rhodozyma*, or chemically synthesized astaxanthin. As a comparison, the flesh of wild Atlantic salmon on average contain 5 ppm of astaxanthin, Coho salmon about 14 ppm astaxanthin and sockeye salmon average 40 ppm (Turujman, 1997). Since astaxanthin from Haematococcus is typically provided at 1-mg dosages in dietary supplements, each gelcap has an amount of astaxanthin equivalent to that present in 200 grams of Atlantic salmon.

Astaxanthin

A growing body of scientific literature reveals significant evidence that astaxanthin surpasses the antioxidant benefits of beta-carotene, zeaxanthin, canthaxanthin, vitamin C, and vitamin E. Animal studies have also shown that astaxanthin can protect skin from the damaging effects of ultraviolet radiation, ameliorate age-related macular degeneration, protect against chemically induced cancers, increase high density lipoprotein and enhance the immune system. Much of the research conducted on astaxanthin has been performed in Japan. The research and interest in astaxanthin in Japan is evidenced by the patents that have been issued, including two for external preparations for the skin, Japanese patent No.'s 0807331, and 08073312, one concerning astaxanthin as an anti-inflammatory agent, Japanese patent No. 07300421, and one for an astaxanthin-containing drink mixture, Japanese patent No. 10155459.

The astaxanthin molecule has two asymmetric carbons located at the 3 and 3" positions of the benzenoid rings on either end of the molecule. Different enantiomers of the molecule result from the exact way that the hydroxyl groups (—OH) are attached to the carbon atoms at these centers of asymmetry. If the hydroxyl group is attached so that it projects above the plane of the molecule it is said to be in the R configuration and when the hydroxyl group is attached to project below the plane of the molecule it is said to be in the S configuration. Thus the three possible enantiomers are designated R,R', S,S' and R,S' (meso). Free astaxanthin and its mono- and diesters from Haematococcus have optically pure (3S,3'S)-chirality (Grung et al., 1992 and Renstrom et al., 1981).

Astaxanthin, is biosynthesized through the isoprenoid pathway, which is also responsible for the vast array of lipid soluble molecules such as sterols, steroids, prostaglandins, hormones, vitamins D, K and E. The pathway initiates at acetyl-Co-A and proceeds through phytoene, lycopene, β-carotene, and canthaxanthin before the last oxidative steps to astaxanthin. Fatty acids are esterified onto the 3' hydroxyl group(s) of astaxanthin after biosynthesis of the carotenoid, and allow it to have more solubility and stability in the cellular environment.

Prior Research

Humans have developed sophisticated systems of arteries, veins and capillaries to deliver and regulate oxygen-rich blood to every cell of the body. Although oxygen is required for normal metabolic activity, it also presents severe challenges to cells. Harmful species of oxygen such as singlet oxygen and free radicals are commonly formed as a consequence of photooxidation, physiological stress and normal immune system functions. These highly unstable molecules contain unpaired electrons that cause cellular injury such as amino acid oxidation, protein degradation, and DNA damage. Free radicals also have an inordinate affinity to attack unsaturated fatty acids, the principle component of cell membranes. These peroxidized fatty acids then create more fatty acid radicals in a chain reaction. Due to its particular molecular structure, astaxanthin has both a very potent neutralizing or "quenching" effect against singlet oxygen as well as a powerfil scavenging ability for free radicals and serves as an extremely effective antioxidant against these reactive species (Kurashige et al. 1990; Jorgensen, 1993; Miki, 1991, Di Mascio, 1989, Terao, 1989). We normally have a balance of free radicals and an arsenal of antioxidants to counter them, but poor nutrition or disease can upset this equilibrium. A number of theories suppose that an upset oxidative balance can be a contributing factor in such conditions as rheumatoid arthritis, heart disease, Parkinson's disease, Alzheimer's disease, cancer and stroke.

Although researchers use different assay systems, astaxanthin has been shown to surpass the antioxidant activity of other carotenoids such as zeaxanthin, lutein, beta-carotene and canthaxanthin. Astaxanthin has an activity over 500 times greater than alpha-tocopherol, also known as vitamin E (Di Mascio, 1989; Ranby and Rabek 1978; Shimidzu, 1996). One prominent researcher has proposed astaxanthin as the "super vitamin E" (Miki, 1991).

Researchers have developed a variety of methods to measure the antioxidant capacity of carotenoids. Some of these assays are conducted in test tubes (in vitro) to better control conditions or within cells themselves (in vivo). Typically, a chemical that generates free radicals or peroxides is mixed with a substrate such as a fatty acid that can become readily oxidized. When the reaction rate is determined, carotenoids or other antioxidants can then be added to determine how they quench, or slow the peroxidation rate of the fatty acid.

Numerous studies exist demonstrating the potent radical scavenging and singlet oxygen quenching properties of astaxanthin (Haila, 1997;Woodall, 1997;Nakagawa, 1997;Oshima, 1993; Tinkler, 1994). It has been demonstrated that astaxanthin is significantly more effective in neutralizing free radicals than beta-carotene and protects against peroxidation of unsaturated fatty acid methyl esters better than canthaxanthin, beta-carotene or zeaxanthin (Terao, 1989; Jorgensen, 1993). In fact, the antioxidant activities of astaxanthin have been shown to be approximately 10 times stronger than other carotenoids such as zeaxanthin, lutein, canthaxanthin, and beta-carotene (Miki, 1991).

The unique structure of astaxanthin scavenges lipid radicals and effectively breaks peroxide chain reactions (Terao, 1989). Di Mascio utilized a chemiluminescent technique to express the superior singlet oxygen quenching ability of astaxanthin compared to other carotenoids. He also concluded that the effectiveness and potency of astaxanthin was even better expressed at the lower oxygen concentrations found in tissues, as opposed to higher oxygen concentrations normally used with in vitro conditions (Di Mascio, 1989). Many antioxidant studies are conducted under conditions of low vitamin E (tocopherol) or vitamin A to better assess the actual effects of the added carotenoids. The antioxidant activity of astaxanthin is even greater than vitamin E (Kurashige, 1990). In vitamin E-deficient rats, astaxanthin protects the mitochondria from damage caused by lipid peroxidation.

Epidemiological studies have demonstrated a correlation between increased carotenoid intake and the reduced incidence of coronary heart disease and certain cancers, macular degeneration, and increased resistance to viral, bacterial, fungal and parasitic infections (Seddon, 1994; Zhang, 1999, Rao, 1999; Rumi, 1999; Batieha, 1993). Studies indicate that the mechanism for this protective attribute is partly due to the direct enhancement of the immune response by carotenoids. Anticarcinogenic effects of carotenoids are likely attributable to its antioxidant effect, insofar as oxygen radicals are related to the process of cancer initiation and propagation.

A synopsis of these studies demonstrates that supplementation with carotenoids increases the number of circulating lymphocytes (T-helper cells), enhances T and B lymphocyte proliferation, improves rejection of foreign tissue, increases killer cell destruction of tumor cells and neutrophil killing of Candida fungi, and inhibits loss of macrophage receptors (Bendich, 1990). Mice fed carotenoids had significantly reduced tumor growth when the primary lesion was excised and then re-challenged with the same tumor (Tomita, 1987). Virus-induced tumors such as murine sarcoma are slowed by carotenoids, as well as adenocarcinoma, squamous cell carcinoma, fibrosarcoma, and chemically induced tumors (Bendich, 1990). These studies present strong evidence that orally administered carotenoids can directly affect the immune responses to cancerous tumors and lead to a lower tumor burden.

Typically, various chemicals are used to induce specific cancers in rats or mice and different dietary supplements are added or left out to test their effects. In rats, the chemical azoxymethane has been used to induce colon cancer and study the effect of anticancer agents. The incidence and multiplicity of neoplasms in the large intestines were significantly smaller after rats were fed astaxanthin. The authors suggest that astaxanthin is a possible chemopreventer of colon, bladder and oral carcinogenesis due to the suppression of cell proliferation (Tanaka, 1995a). Chemically induced mice also had a significantly reduced incidence of preneoplastic lesions and neoplasms in the bladder when given 50-ppm dietary astaxanthin in drinking water. The researchers suggest that astaxanthin is a possible chemopreventive agent for bladder carcinogenesis and such an effect is partly due to suppression of cell proliferation (Tanaka, 1994). Further studies reported incidences of preneoplastic and neoplasms in the oral cavity of rats were significantly smaller when they received 100-ppm dietary astaxanthin after the carcinogenic chemical induction. In particular, no oral neoplasms developed when rats were fed astaxanthin and the chemical inducer at the same time. In other studies rats were induced with a chemical to initiate hepatocarcinogenesis (liver cancer), dietary astaxanthin was found to have a significant influence on the reduction in number and size of neoplastic liver lesions (Astorg, 1997).

Astaxanthin has also been shown to reduce the carcinogenicity of aflatoxin by inducing enzymes called "CYP1A" and "CYP1A2" which enhance diversion of toxic byproducts towards detoxification pathways (Gradelet, 1997). At dietary levels of 300 ppm, astaxanthin is a strong inducer of CYP1A1 and CYP1A2. (Gradelet, 1996b). In contrast to lycopene or vitamin A, astaxanthin was very efficient in reducing the number and size of liver preneoplastic foci in aflatoxin-induced carcinogenesis (Gradelet, 1998).

In one other applied study, mice fed astaxanthin-rich egg yolks developed only one third as many neoplasms and less incidence compared to the control when stomach tumorigenesis was initiated with chemicals (Lee Sang, 1997).

Singlet oxygen is also cytotoxic to the immune system by virtue of its ability to catalyze production of free radicals. This action can facilitate degradation of macrophage cell membranes resulting in dysfunction and reduced efficiency of phagocytosis (Bendich, 1991). Carotenoids have been shown to enhance both the non-specific and specific immune system and protect cell membranes and cellular DNA from mutation (Bendich A. 1989). Carotenoids have a significant stimulatory effect on the immune system, as seen by the proliferative response of spleen cells and thymocytes during antibody response of mice. Astaxanthin enhances the release of interleukin-1 alpha and tumor necrosis factor alpha in mice greater than canthaxanthin and beta-carotene. The conclusion of one study was that astaxanthin had the best cytokine-inducing activity and may provide an immunomodulating role (Okai, 1996).

A key regulator of the immune system is T-helper (Th) cells which are mainly activated by antigens foreign bodies presented by antigen presenting cells (APC's). IgM antibody is produced during the early response to a foreign microorganism or antigen and is restricted to the bloodstream. IgG is the most abundant type of circulating antibody and can traverse blood vessels.

In one series of immune system challenges, astaxanthin enhanced T-helper cell antibody production even when suboptimal amounts of antigen were present. Furthermore, astaxanthin, but not other carotenoids (canthaxanthin, beta-carotene, lutein, lycopene), increased the number of antibody-secreting cells from primed spleen cells (Jyonouchi, 1996). Using human blood, it was shown that astaxanthin enhances the production of IgM, IgA and IgG antibodies in response to T-dependent stimuli (Jyonouchi, 1995a and 1995b). Another study indicates a significant immunomodulating action of astaxanthin for humoral immune responses to T-dependent antigens and the authors suggest that carotenoid supplementation may be beneficial in restoring humoral immune responses in older animals. Furthermore, it was speculated that dietary carotenoids could reduce the chance of developing autoimmunity and malignancies by enhancing T-helper functions and promoting specific antibody responses (Jyonouchi, 1994).

Another study indicates a significant immunomodulating action of astaxanthin for humoral immune responses to T-dependent antigens and the authors suggest that carotenoid supplementation may be beneficial in restoring humoral immune responses in older animals. Furthermore, it was speculated that dietary carotenoid could reduce the chance of developing autoimmunity and malignancies by enhancing T-helper functions and promoting specific antibody responses (Jyonouchi, 1994).

Another study involved monocytes, which are a particular type of white blood cell which contain surface proteins that distinguish cancer cells from normal healthy ones. When these MHC II proteins identify cancer cells they signal the immune system to attack them. Monocytes do not identify cancer cells if they don't have enough MHC II proteins. It was demonstrated that supplementation with a carotenoid in diets increase the number of MHC II proteins on monocytes. In turn, subjects had increased production of tumor necrosis factor alpha (TNF-a) which helps kills cancerous and virus-infected cells (Hughs, 1997).

Additional work has used an oral preparation of Haematococcus algae as an agent for ameliorating ulcers when the causative agent is Helicobacter bacteria. It appears that Helicobacter itself does not cause peptic ulcer, but the inflammation of the stomach lining in response to the bacteria. In the United States, Helicobacter affects about 20% of persons below the age of 40 years, and 50% of those above the age of 60 years. Although the exact mechanism has not been established, astaxanthin from Haematococcus can presumably neutralize the superoxide radicals and augment the immune system such that the Helicobacter can be controlled by the immune system.

Ultraviolet radiation has long been known to cause epidermis photoaging and skin cancer, and special SKH 1 hairless mice sensitive to UV light are often used to understand the effects of antioxidants and light-induced polyamines. Polyamines are central to normal growth and activation of polyamine metabolism, and putrescine in particular is involved in tumor promotion. In one study, female SKH1 hairless mice were weaned at eight weeks and fed six different diets containing 5 ppm beta-carotene, 10 ppm astaxanthin or retinol. After 4 months, one half of each group was exposed to ultraviolet light, sacrificed, and putrescine concentrations measured in the epidermis. After irradiation, astaxanthin alone or in combination with retinol was remarkably effective in preventing increases of free putrescine after damage was induced. The putrescine of the control group increased 4.1-fold whereas the groups fed astaxanthin increased only 1.5-fold. Astaxanthin also had a stronger inhibitory effect on putrescine accumulation than retinol, and decreased spermidine and spermine concentrations, which suggests a specific action on transglutaminase enzymes (Savoure, 1995).

In rat kidney fibroblasts, addition of astaxanthin exhibits superior protection against UVA light-induced oxidative stress compared to lutein and beta-carotene. Cell cultures were grown in carotenoid-supplemented media and exposed to UVA light for four hours at which time various parameters were assayed. Beta-carotene at a level of 1000 nM and lutein at 100 nM returned catalase activity to control levels whereas it only required 5 nM of astaxanthin. Levels of 500 nM beta-carotene, 1000 nM of lutein and only 5 nM of astaxanthin were required to restore the superoxide dismutase activity of UVA-exposed cells. Thiobarbituric acid reactive substances (TBARS) were also measured as indices of oxidative stress. Supplementation of beta-carotene at 100 nM, lutein at 1000 nM and astaxanthin at only 1 nM prevented the UVA-induced increase in TBARS (O'Connor, 1998).

In cell culture studies, similar results demonstrate the efficacy of astaxanthin as an antioxidant and chain-breaking molecule in the peroxidation of membrane phospholipids (Lim, 1992). In one report, primary cultures of chicken embryo fibroblasts (CEF) were oxidatively stressed by exposure to paraquat (radical generator) and various levels of astaxanthin were added to ascertain the antioxidant effect. Activities of the antioxidant enzymes superoxide dismutase (SOD), catalase and glutathione peroxidase were measured as indices of oxidative stress. Without astaxanthin, paraquat increased the activities of SOD and catalase more than two-fold, and decreased the activity of glutathione peroxidase by more than 50% indicating high oxidative stress. Protection against paraquat-induced oxidative stress was observed at all levels of astaxanthin tested, demonstrating its effectiveness as an antioxidant in this model (Lawlor and O'Brien, N. M., 1994). Astaxanthin furnishes more protection to rat liver microsomes undergoing radical-initiated lipid peroxidation than either beta-carotene or vitamin E (Palozza, 1992; Nishigaki, 1994).

Metabolic Effects of Astaxanthin

High-density lipoprotein (HDL) is a complex of lipids and proteins that functions as a transporter of cholesterol in the blood. Higher levels of HDL "good cholesterol" and lower levels of LDL "bad cholesterol" are associated with a decreased risk of atherosclerosis and coronary heart disease. In one study, male Wistar rats fed 0.1% dietary astaxanthin for 30 days had increased HDL cholesterol of 57 mg/dL compared to the control diet with 42.4 mg/dL. Conversely, the LDL bad cholesterol decreased from the control diet of 12.5 mg/dL to 9.6 mg/dL when supplemented with astaxanthin. Neither beta-carotene nor canthaxanthin elicited the same effect. Additional studies are in progress, but it is can be speculated that astaxanthin or other carotenoids can decrease the oxidation of these lipid-carriers and thereby reduce the risk of atherosclerosis (Murillo, 1992).

Astaxanthin may also have a physiological benefit in energy metabolism. Dr. Curt Malmsten conducted a double-blind study at the Paramedical School of Vrmd (Gustavsberg, Sweden) in which 40 healthy students were divided into two groups for a series of physiological tests with and without astaxanthin supplementation. The students were given either a placebo capsule or one with 2 mg of astaxanthin from Haematococcus algae. At the end of six months, there was a not a significant difference in the hemoglobin values between the two groups but there was a significant difference in the strength/endurance that was measured by knee bends and a barbell weight. The results showed the placebo group reached on average score of 21.78 and the experimental group attained 61.74 on average ($P=0.047$).

It is interesting to note that in stress experiments conducted with shrimp, survival is higher in those fed a diet containing astaxanthin. The positive correlation between survival and pigment concentration of tissues suggests that astaxanthin can function as an intracellular oxygen reserve which permit crustaceans to survive under anaerobic conditions common in pond cultures. After 3 months, shrimp fed astaxanthin at 50 mg/kg diet had an average survival rate of 87%. In contrast, there was 50% survival when shrimp were deprived of carotenoids or supplemented with 50 mg/kg of -carotene (Chien, 1992). One may surmise that astaxanthin may have positive benefits for endurance during aerobic activities when muscles are demanding oxygen.

Atlantic salmon have the distinction as being the species for which astaxanthin has been shown to be an essential vitamin, with absolute minimum levels being about 5.1 ppm. A recent groundbreaking study in Norway by Christiansen and his colleagues demonstrated that Atlantic salmon fry have a definitive growth and survival requirement for astaxanthin in their diet. Fish fed diets with astaxanthin below 5.3 ppm were found to have marginal growth, those fed levels above 5.3 ppm had significantly higher lipid levels accompanied by lower moisture levels. When fry were fed astaxanthin concentrations below 1 ppm, survival rates plummeted to less than 50% whereas survival of groups receiving higher concentrations had survival rates greater than 90% (Christiansen et al., 1995).

GAP junctions are relatively non-specific pores that connect two cells and are "gated" such that they can open or close in response to certain stimuli. These functions are especially important in the propagation of nerve impulses. Carotenoids are known to protect cells against chemically induced carcinogenic transformations through the enhancement of GAP junctional communication between cells. Chemoprevention activity strongly correlates to the expression of the gene, connexin43, coding for a GAP junctional protein (Bertram J. S. et al., 1991). GAP junctional communication (GJC) has been linked to increased growth control, chemopreventive carotenoids increase expression of this gene and act as potential chemoprotective agents (Zhang L. X. et. al.1991; King T. J. et.al. 1997). This has led to the theory that carotenoids enhance or expand GAP junction communication which serves as a conduit for growth regulatory signals (Bertram, 1991; Zhang et al, 1992). The effect on GAP junctions is also partly explained by the finding that astaxanthin functions as a membrane stabilizer, essentially acting as trans-membrane rivets between lipid bilayers (Woodall, 1997; Milon, 1986).

Support of Eye Health

In humans and other animals, carotenoids are essential for proper health of the eye, a number of studies have demonstrated that dietary carotenoids help to protect the retina against oxidative damage (Snodderly, 1995). The macula is the small central part of the retina encompassing an area of about 2 millimeters in diameter directly behind the lens of the eye. This region produces the sharp vision need to read and see fine details clearly. The retina contains the highest concentration of polyunsaturated fatty acids of any tissue in the human body and a particularly high level of oxygen. When high-energy blue light waves interact with the retina they can cause peroxide damage of the lipids through photo-oxidation, which in turn creates singlet oxygen and free radicals. Carotenoids within the macula absorb the high energy blue light thereby quenching these damaging oxygen species. Clinical studies have indicated that light injury is a major cause of a disease called "age-related macular degeneration" (AMD) because of this cumulative light insult. AMD results in a gradual loss of photoreceptor cells and is the leading cause of irreversible blindness among older Americans that have decreased levels of carotenoids in their eyes.

Unlike beta-carotene, astaxanthin is able to readily cross the blood-brain barrier and protect the retina against photo oxidation and loss of photoreceptor cells. Astaxanthin has not been shown to crystallize in the retina, though this has been reported to cause asymptomatic indications with canthaxanthin in the past. Furthermore, astaxanthin has the ability to protect the neurons of the retina as well as those of the central nervous system, especially the brain and spinal cord, from damage caused by free radicals (Seddon et al. 1994; U.S. Pat. No. 5,527,533).

In animal tests, seven albino Lewis rats were first fed a normal diet and placed on a twelve hour cycle of light and darkness for 14 days. Four rats were then administered intraperitoneal injections of astaxanthin corresponding to 37.5 mg astaxanthin/kg of body weight at 12 hour intervals. All seven rats were then exposed to 180–200 ft-candle (1800–2000 lux) green-filtered fluorescent light at 490–580 nm for 24 hours. The rats were then kept in the dark for a two-day recovery period and euthanized for analysis of the retinas. By measuring the thickness of the outer nuclear layer (ONL) of the retina, a quantitative determination of the photoreceptor cell degeneration could be made. It was found that control rats without treatment or photic injury had an ONL measurement of 45 microns, whereas the group receiving photic injury without astaxanthin supplementation had an ONL measure of 32 microns. The ONL measurement of rats receiving astaxanthin and photic injury had an ONL measurement of 42 microns, which showed that administration of the carotenoid provides a significant protection to receptor cells from photic injury. The astaxanthin protected the photoreceptors in each eye of the four quadrants and in the whole eye as well.

A similar follow-up study was conducted with oral dosing of astaxanthin to measure the effects of photic injury on rhodopsin levels in the eye. It was found that rhodopsin levels in the retinas of control rats fell for six days following photic injury, then began to recover. After 6 hours of photic injury, the rhodopsin level of control rats was 0.75 nmol, and continued to decrease to 0.5 nmol after 6 days. The level improved to 0.8–0.85 nmol after 13 days from the initial photic insult. In contrast, the astaxanthin-treated rats had a rhodopsin level of about 1.15–1.2 nmol at the 6-hour post injury stage. Additionally, the rhodopsin did not decrease over the subsequent 6 days, but increased to a level of about 1.25 nmol and remained essentially constant through day 13 after photic injury. The authors state that the astaxanthin not only protects the receptor cells from photic injury but also ameliorates the effects of the damage since the rhodopsin levels never decrease, but rather increase over the recovery period (U.S. Pat. No. 5,527,533).

The references cited herein are incorporated by reference into the background of the invention.

Thus, it would be desirable to find a treatment or cure for fever blisters and canker sores incorporating the protective properties of astaxanthin.

SUMMARY OF THE INVENTION

Astaxanthin is a potent antioxidant, over 500 times more powerful than Vitamin E and 10 times stronger than other carotenoids such as zeaxanthin, lutein, canthaxanthin and beta-carotene. Astaxanthin has also been shown to enhance and modulate the immune system and diminish the damaging effects of UVA sunlight. These effects in combination or separately can retard or ameliorate fever blisters and canker sores when astaxanthin is ingested and/or applied topically in a therapeutically effective dose.

Thus one aspect of the invention is to produce an inexpensive treatment or cure for fever blisters and canker sores.

Another aspect of the invention is to provide an ingestible treatment or cure for fever blisters and canker sores.

A still further aspect of the invention is to provide a topical treatment or cure for fever blisters and canker sores.

A further aspect of the invention is to use the unique antioxidant properties of astaxanthin to retard or ameliorate fever blisters and canker sores.

A still further aspect of the invention is to provide a therapeutically effective dose of ingestible astaxanthin in the range of about 1–100 mg per day to retard or ameliorate fever blisters and canker sores.

These and further aspects of the invention will be shown as illustrated in the is following detailed description of the invention, and the appended claims.

DETAILED DESCRIPTION OF THE INVENTION

Advanced technology has been developed to grow the algae Haematococcus in closed culture systems and harnesses the unique properties of the algae to produce very high concentrations of natural astaxanthin. All media ingredients for the cultivation of the algae are food grade or higher quality and the algae is pasteurized to prevent microbial contaminants. No solvents, pesticides, herbicides or toxic substances are used during cultivation or manufacturing of the product. Lots are standardized to contain from 1.5% (15,000 ppm) astaxanthin, predominately in the esterified form that provides the highest stability. Other beneficial carotenoids such as β-carotene, canthaxanthin, and lutein are also present in lesser amounts. Most importantly, the production process includes a technique which "cracks" greater than 95% of the algae cells to enable maximum bioavailability, resulting in a fine dark red powder.

Dried Haematococcus algae, Phaffia yeast powder, or synthetic astaxanthin can be formulated into various food grade oils such as safflower, canola, tocopherols or rice bran, and manufactured into gelcaps for convenient ingestion. Alternatively, dried Haematococcus algae, Phaffia yeast powder, or synthetic astaxanthin can be stabilized by various commercial processes and added directly to foods or beverages. Astaxanthin is currently used as a general dietary supplement, in the various formulations discussed above, to take advantage of its potent antioxidant properties to, among other uses, enhance and modulate the immune system and counteract the damaging effects of UVA sunlight. Astaxanthin from Haematococcus may be provided at 1-mg gelcap dosages in general dietary supplements, and each gelcap has an amount of astaxanthin equivalent to that present in 200 grams of Atlantic salmon.

Astaxanthin from Haematococcus algae or other sources can also be formulated into an oil or cream ointment and used as a direct topical treatment for the lips or other tissue. This form directly counteracts the effect of UV irradiation from the sun and provides antioxidants directly to the tissues.

Safety Studies of Haematococcus Algae Meal

Animal studies have proven the safety of consuming Haematococcus algae. It has never been associated with any toxicity in the reported literature or in field studies. Haematococcus algae has been reviewed by the US FDA and allowed as a new dietary ingredient by means of the DSHEA (21 CFR 190.6). It has also been approved in Japan for use in both foods and animal feeds. A different formulation of Haematococcus algae has already gained wide acceptance in the aquiculture markets as a pigmentation and vitamin source for salmon, trout, shrimp and ornamental fish and has been approved as a feed additive for salmonids by the Canadian Food Inspection Agency. Similar registrations are in progress, by Applicant, in the United States by the FDA and the European Union.

A number of standard toxicity and safety studies have been conducted with Haematococcus algae. Acute oral toxicity studies were conducted on Charles River CD rats with a dosage level of 5 grams of Haematococcus algae/kg for 13 days. Groups were evaluated for mortality, pharmacotoxic signs, body weights, and necropsy examinations during the 13-day study. The results demonstrated that the $LD_{50}$ value of each lot was greater than the administered dose of 5 grams/kg. No visible abnormalities were observed, nor differences in body weights during the study. The postmortem examination did not reveal any abnormalities in rats sacrificed at the end of the study. A second clinical acute toxicity study with rats showed a $LD_{50}$ value higher than 12 grams/kg with no clinical, weight or behavioral abnormalities. The post-mortem pathology showed no appreciable macroscopic findings at the end of the 14 days. Hematology, blood chemistry, urinalysis, organ weight, and gross pathology were all clinically normal.

Higher dosage studies of acute oral toxicity have been conducted with both male and female mice ranging from 10.4–18.0 grams Haematococcus algae per kg of body weight with no mortalities or abnormalities observed at the end of the study. Mutagenicity tests under standard conditions are negative for Haematococcus algae. Another published study with rats fed 400 ppm astaxanthin for 41 days showed no harmful effects on body/organ weight, enzyme activities, pregnancy, or litter size (Nishikawa et al., 1997).

Thus, there is every indication that Haematococcus algae is a safe and natural form of astaxanthin that has been shown to have excellent antioxidant properties beyond other carotenoids. Positive outcomes in cancer deterrence, immune enhancement and macular degeneration studies are likely related to these superior antioxidant properties as well as yet unknown mechanisms.

EXAMPLE 1

Haematococcus algae meal containing 1.5% astaxanthin was thoroughly mixed with safflower oil such that the resulting suspension contained 2.0 mg of pure astaxanthin per gram of safflower oil suspension. 500 mg soft gel capsules were produced from the safflower oil suspension such that each soft gel capsule contained 1.0 mg of pure astaxanthin.

One individual was a 50 year-old male who has suffered from cold sore outbreaks every 4–6 weeks on average which lasted 10–14 days. This individual consumed 3.0 mg of astaxanthin (three soft gel capsules) per day for two weeks prior to an outbreak, and the symptoms lasted only 2 days instead of 2 weeks. The individual has not had a another recurrence of cold sores in three months since ingesting the astaxanthin.

EXAMPLE 2

A second individual was a thirty-five year-old male who had often suffered canker sores on the inside of his mouth since the age of about 12 years old. He had difficulty and pain eating sour and tart foods due to the condition. This individual consumed 2.0 mg of astaxanthin (two soft gel capsules) per day for three weeks and the cankers sores were alleviated. He was then able to eat sour and tart foods without suffering pain from the canker sores. When the individual stopped taking the supplement the canker sores returned within 10 days. However, when the individual then took the supplements again at the same dosage, the symptoms were ameliorated after approximately three weeks and did not return as long as he continued to ingest the astaxanthin.

While there exists a body of research on fever blisters, a body of research on canker sores, and a body of research on carotenoid and astaxanthin, none of the research suggests using an oral or topical dosage delivery of astaxanthin for the treatment and amelioration of fever blisters or cold sores.

Thus one embodiment of the invention is a method of treating fever blisters and canker sores, by orally administering a therapeutically effective dose of astaxanthin. The astaxanthin retards and ameliorates the fever blisters and canker sores. The desired therapeutic dose may be in the range between about 1 to about 100 mg of astaxanthin orally per day, preferably in range of about 1 to about 50 mg orally per day, or in the range of about 2 to about 5 mg orally per day.

Another embodiment of the invention is a method of treating fever blisters and canker sores, by topically administering a therapeutically effective dose of astaxanthin to the tissue where one or more fever blisters and/or canker sores is present. The astaxanthin retards and ameliorates the fever blisters and canker sores. The desired therapeutic dose may be in the range between about 1 to about 100 mg of astaxanthin topically per day.

The astaxanthin may be administered orally, topically, or in a combination of an oral and topical dosage.

The preferred form of astaxanthin to be administered is a form esterified with fatty acids. Preferably the astaxanthin used is derived from natural sources such as Haematococcus algae, or Phaffia yeast powder, but chemically synthesized astaxanthin may also be used. Thus, the present invention provides a relatively inexpensive, effective method of treating fever blisters and canker sores.

What is claimed is:

1. A method to retard, ameliorate, and prevent canker sores, comprising orally administering a therapeutically effective dose of astaxanthin.

2. The method according to claim 1 wherein said therapeutically effective dose is in the range of about 1 to about 100 mg of astaxanthin per day.

3. The method according to claim 2 wherein said therapeutically effective dose is in the range of about 1 to about 50 mg of astaxanthin per day.

4. The method according to claim 3 wherein said therapeutically effective dose is in the range of about 1 to 10 mg of astaxanthin per day.

5. The method according to claim 1 wherein said astaxanthin is in a form esterified with fatty acids.

6. The method according to claim 1 wherein said astaxanthin is derived from natural sources.

7. The method according to claim 6 wherein said natural sources are Haematococcus algae, or Phaffia yeast powder.

8. The method according to claim 1 wherein said astaxanthin is produced synthetically.

9. A method to retard and ameliorate canker sores comprising topically administering a therapeutically effective dose of astaxanthin to the tissue where a canker sore is present.

10. The method according to claim 9 wherein said therapeutically effective dose is in the range of about 1 to about 100 mg of astaxanthin per day.

11. A method to retard, ameliorate, and prevent canker sores comprising orally administering a therapeutically effective dose of astaxanthin to a patient having one or more canker sores, in combination with topically administering a therapeutically effective dose of astaxanthin to the tissue where a canker sore is present.

12. The method according to claim 4 wherein said therapeutically effective dose is in the range of about 2 to 5 mg of astaxanthin per day.

\* \* \* \* \*